(12) United States Patent
Cheng et al.

(10) Patent No.: US 8,328,356 B2
(45) Date of Patent: Dec. 11, 2012

(54) ENABLING MEASUREMENT WITH A HANDHELD EYE IMAGING DEVICE

(75) Inventors: Yeou-Yen Cheng, Saratoga, CA (US); Barry Linder, Danville, CA (US); Willem Crone, Oroville, CA (US); Yan Zhou, Pleasanton, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 136 days.

(21) Appl. No.: 12/606,041

(22) Filed: Oct. 26, 2009

(65) Prior Publication Data

US 2010/0110378 A1    May 6, 2010

Related U.S. Application Data

(60) Provisional application No. 61/111,968, filed on Nov. 6, 2008.

(51) Int. Cl.
*A61B 3/14* (2006.01)
*A61B 3/10* (2006.01)

(52) U.S. Cl. .......... 351/208; 351/206; 351/211
(58) Field of Classification Search .......... 351/208, 351/205, 206, 211, 221
See application file for complete search history.

(56) References Cited

U.S. PATENT DOCUMENTS 6,145,990 A * 11/2000 Uchida .......... 351/221

* cited by examiner

*Primary Examiner* — Jack Dinh
(74) *Attorney, Agent, or Firm* — Charles E. Krueger

(57) ABSTRACT

An apparatus and method is disclosed that enables an existing handheld eye imaging device to do direct measurement on images taken from the patient eye. In a preferred embodiment, a reticle is arranged in the handheld eye imaging device so that a reticle image is superimposed on the object image. In addition to allowing the user to make measurements, the reticle superimposed eye image can also be used to align the eye with the handheld eye imaging device, be used for registering images taken at different times, and also be used for finding previously recorded points on the images for comparison purposes.

17 Claims, 5 Drawing Sheets

Figure 1 shows an example of a reticle image superimposed with the anterior chamber angle image of an eye model.

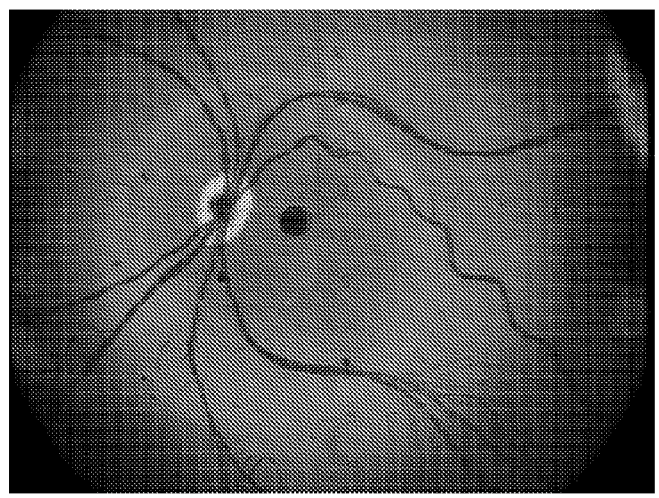
Figure 2 shows an example of A reticle image superimposed with the posterior chamber image of a baby eye model.

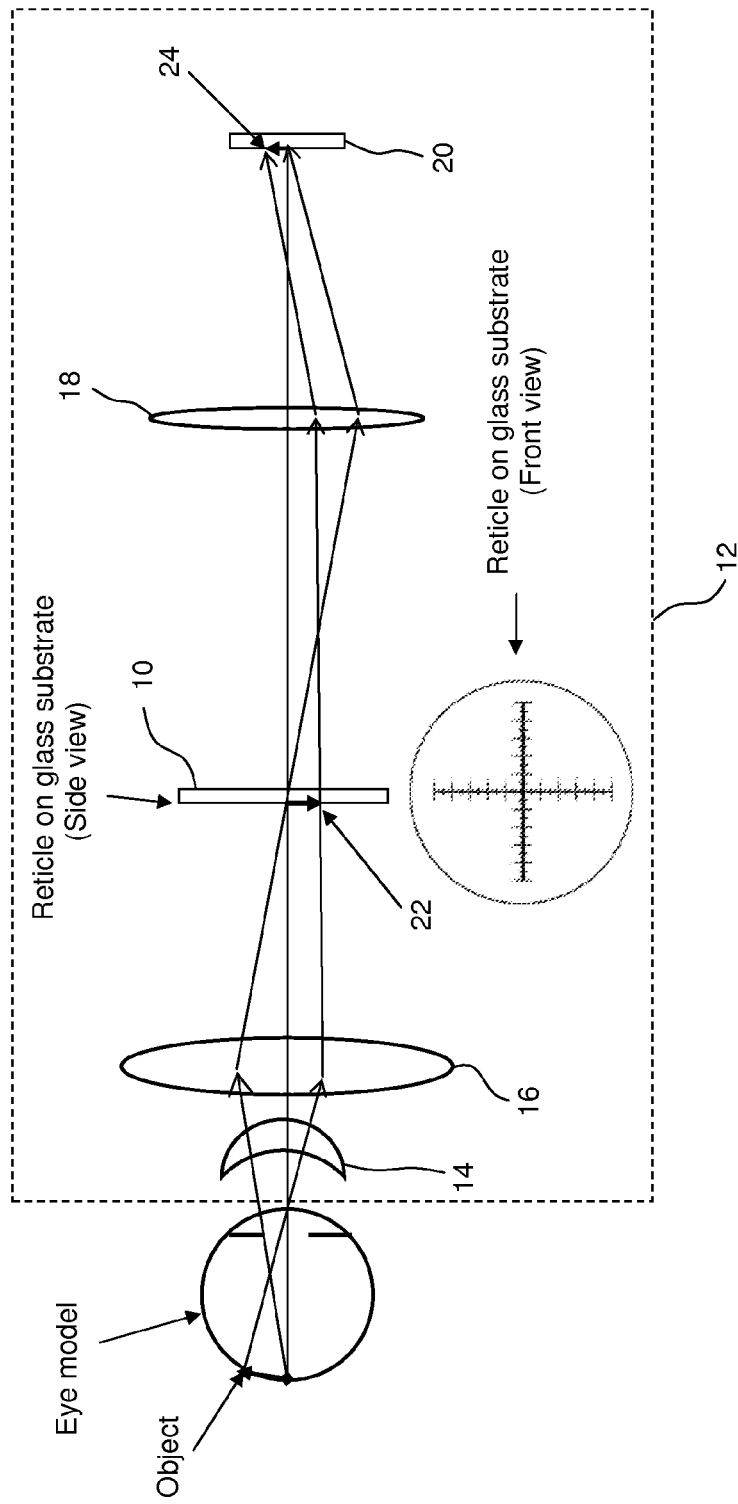
Figure 3 depicts a first example embodiment in which the reticle is self illuminated by the imaging beam.

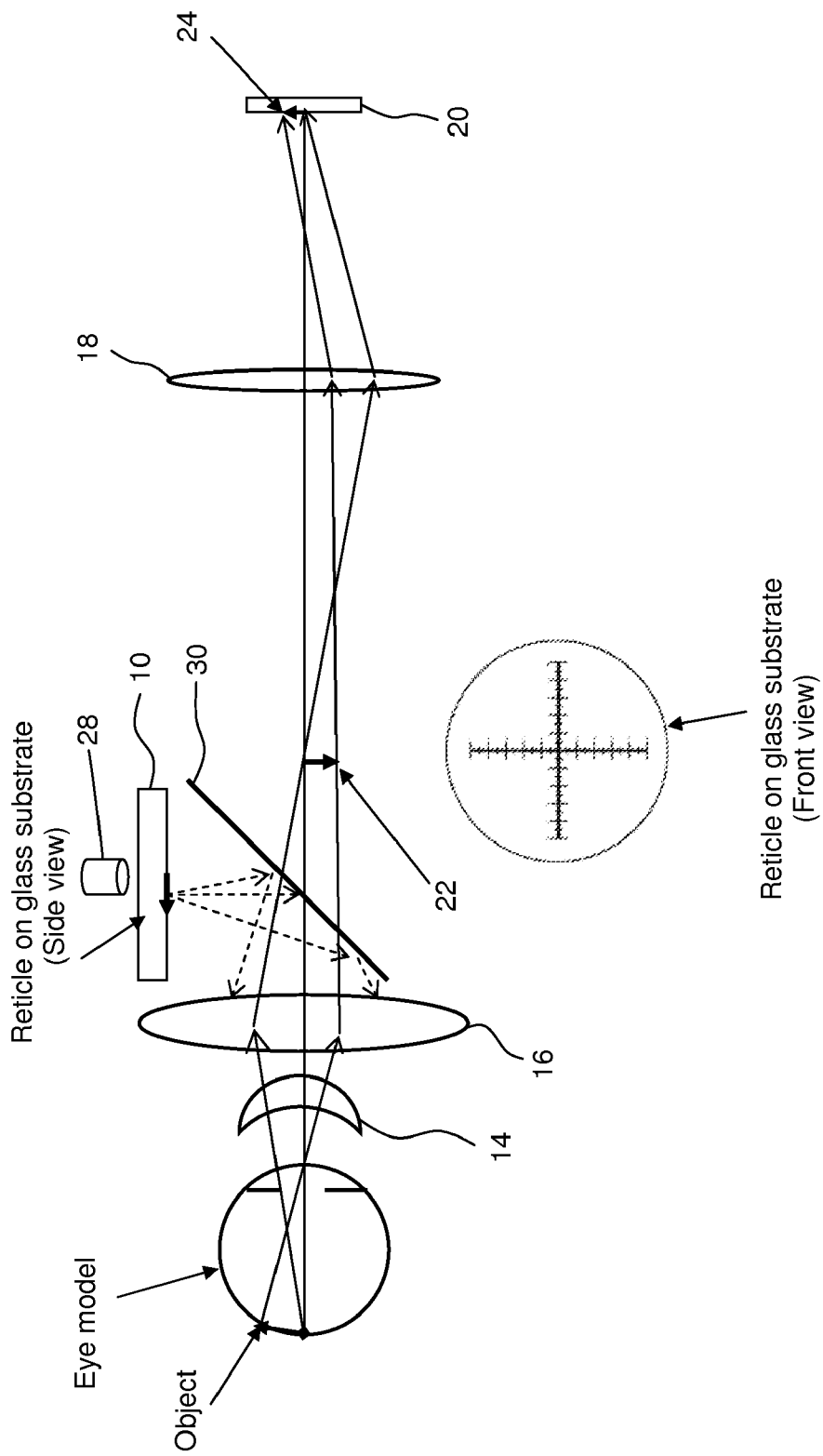
Figure 4 depicts a second example embodiment in which the reticle is projected onto the eye after being reflected from a beam-splitter.

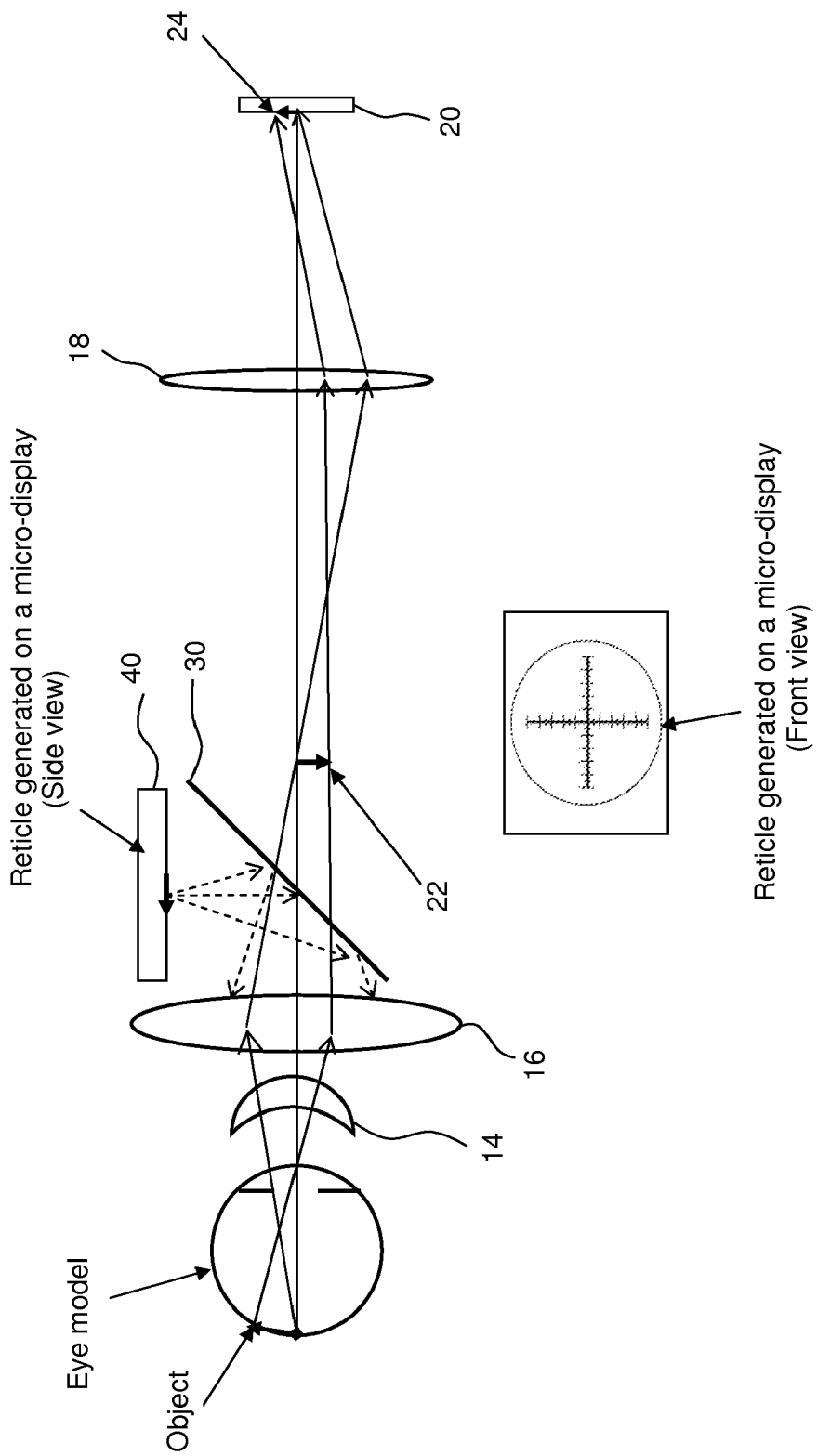
Figure 5 depicts a third example embodiment in which the reticle is generated on a micro-display and then projected on the eye after being reflected from the beam-splitter.

ENABLING MEASUREMENT WITH A HANDHELD EYE IMAGING DEVICE

RELATED APPLICATIONS

This application claims priority from a provisional application entitled APPARATUS AND METHOD ENABLING MEASUREMENT WITH A HANDHELD EYE IMAGING DEVICE, Application No. 61/111,968, filed Nov. 6, 2008, which is hereby incorporated by reference for all purposes.

TECHNICAL FIELD

The present disclosure relates generally to measurement associated with eye examination and imaging.

BRIEF DESCRIPTION OF THE DRAWINGS

FIG. 1 shows an example of a reticle image superimposed with the anterior chamber angle image of an eye model.

FIG. 2 shows an example of a reticle image superimposed with the posterior chamber angle image of a baby eye model.

FIG. 3 depicts a first example embodiment in which the reticle is self illuminated by the imaging beam.

FIG. 4 depicts a second example embodiment in which the reticle is projected onto the eye after being reflected from a beam-splitter.

FIG. 5 depicts a third example embodiment in which the reticle is generated on a micro-display and then projected on the eye after being reflected from the beam-splitter.

DESCRIPTION OF EXAMPLE EMBODIMENTS

Overview

An example embodiment is an apparatus and method that enables an existing handheld eye imaging device to have the capability to do direct measurement on a patient eye or on images taken from the eye. The capability is achieved by attaching a reticle or other measurement pattern(s) to the handheld eye imaging device so that when an anterior or posterior segment image of a patient eye is displayed live or captured, the reticle image is superimposed on the eye image. In addition to allowing the user to make measurements, the reticle image can also be used to align the eye with the handheld eye imaging device, be used for registering images taken at different times, and be used for finding previously recorded points on the images for comparison purposes.

Description

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention. Further, each appearance of the phrase an "example embodiment" at various places in the specification does not necessarily refer to the same example embodiment.

Reticles are generally used in microscopes to help the user to make measurements of the anatomical or pathological details of a biological object being imaged. However, currently there is no handheld eye imaging device that has a reticle incorporated for direct measurement, especially for eye imaging with an optical spectral range beyond the standard visible spectrum. Furthermore, for screening and progressive monitoring of eye disease such as glaucoma and macular degeneration over a relatively long period of disease development and/or curing process, there is a need to at least easily enable the doctor to approximately align the images taken at different times in order to compare the images afterwards, and this need has not been adequately addressed for a handheld eye imaging device.

This example embodiment is an improvement of an established concept. FIG. 3 depicts the incorporation of a reticle 10 into a handheld eye imaging device 12 including a contact type lens 14, an optical relay including first and second lenses 16 and 18 and an image sensor 20. In this example embodiment, an inverted intermediate image 22 of a portion of the retina is formed between the first and second lenses 16 and 18 at a location that is conjugate to both a plane including the object (the retina in this example) and a plane including the image sensor 20. The second lens 18 projects the inverted intermediate image 22 onto the image sensor 20 as a non-inverted minified final image 24 of the portion of the retina. The reticle 10 is positioned at the same location as the intermediate image and is thus conjugate to both the object plane and the digital sensor plane. As described above and as depicted in FIGS. 1 and 2, so that the reticle image can be superimposed onto the image of either the anterior or the posterior segment image of the eye being displayed live or captured for later analysis.

It should be noted that the term reticle is used here to mean any optical element or device or software means that can create lines or marks. Such lines/marks can be simple graduated lines or cross hair lines or circular concentric lines or other patterns created on a thin plate made from glass or optical grade plastics or on the display screen. The reticle can be arranged at any plane as along as it is approximately conjugate to the object plane and the digital image sensor plane. Since the reticle is located at the conjugate plane of the object and the image sensor, a reasonably sharp image of the reticule will be obtained. In other words, when the object being imaged is in good focus, the reticle image will also be in good focus. In the case of a handheld RetCam eye imaging system, the reticle can, for example, be arranged in the lens piece assembly or in the handpiece that holds the digital image sensor. An add-on optical element such as a gonio lens can be further attached to the RetCam lens piece to optimize anterior chamber angle imaging while allowing the reticle image to be superimposed. The reticle can also be separately mounted on an adaptor that can be fixed either on the side of or inside the handheld eye imaging device. Still another possibility is to use software to create a virtual reticle image that is superimposed on the real displayed or captured object image and the dimensions of this virtual reticle image can be controlled based on the focusing condition or the optical magnification of the handheld eye imaging device to always provide a relatively accurate measurement reference.

The reticle image can be directly projected to the digital image sensor without any additional illumination light other than that coming from the object being images as depicted in FIG. 3. It can also be self-illuminated to create better contrast using a separate illuminator such as an LED 28 as depicted in FIG. 4 where the reticle pattern is formed on a glass plate 10 and a virtual image of the reticle pattern is formed on the intermediate image plane by a beam directing element 30. In doing so, an image of the reticle pattern is projected onto the portion of the eye. The relay including first and second lenses 16 and 18 projects the image of the reticle and the portion of the eye to the image sensor 20 so that the image of the reticle overlays the final image 24 of the portion of the eye at the image sensor 20.

Alternatively, the reticle can also be a micro-display with a created image projected onto the digital image sensor. As depicted in FIG. 5, the reticle pattern can be generated by a backlit negative, electro luminescent screen 40 or some other illuminated device and projected onto a relay lens or a beamsplitter 30 configured so that the image generator is at a conjugate plane of the digital image sensor. The reticle image as seen by the user of the handheld eye imaging device can be as simple as a negative image of a reticle with stadia for measurements. Alternatively, it can also display previously recorded images or features to be used for alignment or comparison. Instead of an image, a series of contrast lines can be projected between the pupil and the iris in the eye. The superimposition of these contrast lines can be used to reposition the handheld eye imaging device to a previously recorded image. This would allow similar images to be captured at different times with the same device orientation and position.

This image superposition feature will not only allow the user to do measurement of the anatomical or pathological structure with respect to the measurement reference of the reticle, but also allow the user to refer to features that have been previously recorded onto the region of interest so that the captured image can be aligned to a previously recorded image for a direct comparison.

Another aspect of the present invention is that the projected reticle image can be calibrated to provide improved measurement accuracy. For example, a standardized eye model that has very precise dimension features can be imaged using the reticle containing handheld eye imaging device and the relationship between the projected reticle lines and the actual dimension of the features from the eye model can be established. Following this, the actual size of objects (e.g. apparent width of the trabeculum, size of the optical disc, etc.) can then be relatively accurately obtained.

Still another aspect of the invention is the disclosed method for a handheld eye imaging device to perform measurements of features directly on the live images or images captured of a patient eye with an objective reference (e.g. a reticule pattern, generated with either hardware or software). This method can comprise the steps of superimposing a reticle image with a real anterior or posterior segment image of a patient eye captured by a handheld eye imaging device, and referencing anatomical or pathological features to the reticle to determine the dimension of the features. Additional steps may include digitally recording the combined superimposed images of the object and the reticule or previously recorded image(s); digitally finding the dimension of the anatomical or pathological features, or digitally finding the difference of the currently captured image as compared with previously captured image of the same patient's eye.

In addition to the use of optical radiation within the commonly used visible spectral range, still another aspect of the present invention is the use of optical radiation outside the generally used visible spectrum to image the eye and also project the reticle to the digital image sensor. These optical radiation spectral ranges can be in the ultra-violet, near infrared or even mid infrared and far infrared spectral regions.

The presently disclosed apparatus and method can be applied to any handheld optical imaging system. In addition to optometrist and ophthalmologist practices; the above-described example embodiment can effectively be applied to anywhere as long as the visualization of an eye's anatomy using a handheld eye imaging device is desired.

The invention has now been described with reference to the example embodiments. Alternatives and substitutions will now be apparent to persons of skill in the art. Accordingly, it is not intended to limit the invention except as provided by the appended claims.

What is claimed is:

1. An apparatus for making measurements of a particular portion of a subject eye comprising:
a handheld eye imaging device including a first lens and a second lens and an image sensor with the first lens configured to project an intermediate image of the particular portion of the subject eye to a location between the first and second lenses and with the second lens configured to project the intermediate image onto the image sensor; and
a reticle, having a pattern of lines or other marks formed thereon, positioned substantially at the location of the intermediate image so that both the reticle and the intermediate image particular portion of the subject eye are conjugate to the image sensor, an image of the reticle is projected onto the image sensor by the second lens and where the image of the reticle overlays the image of the particular portion of the subject eye projected onto the image sensor by the second lens to facilitate measurements of the particular portion of the subject eye.

2. The apparatus of claim 1 wherein the reticle comprises a glass plate with marks or lines.

3. The apparatus of claim 1 wherein the handheld eye imaging device is a RetCam eye imaging system.

4. The apparatus of claim 1 further comprising a calibration means to provide improved measurement accuracy.

5. The apparatus of claim 1 wherein imaging is done using optical radiation within the visible spectrum.

6. The apparatus of claim 1 wherein the eye imaging and reticle image projection is done using optical radiation outside the visible spectral range.

7. The apparatus of claim 1 wherein the reticle includes a pattern of thin wires with tick-marks.

8. An apparatus for making measurements of a particular portion of a subject eye comprising:
a handheld eye imaging device including a first and a second lens and an image sensor with the first lens configured to project an intermediate image of the particular portion of the subject eye to a location between the first and second lenses and with the second lens configured to project the intermediate image onto the image sensor;
a reticle pattern formation mechanism having a pattern of lines or other marks formed thereon; and
a beam directing element configured to form a virtual image of the reticle pattern to the location of the intermediate image so that both the virtual image of the reticle and the intermediate image of the particular portion of the subject eye are conjugate to the image sensor, an image of the reticle pattern is projected onto the intermediate image of the particular portion of the subject eye and is relayed to overlay the final image of the portion of the subject eye at the image sensor to facilitate measurements of the particular portion of the subject eye.

9. The apparatus of claim 8 wherein the reticle pattern formation mechanism comprises:

a glass plate with marks or lines; and a light source configured to back illuminate the glass plate.

10. The apparatus of claim 8 wherein the reticle pattern formation mechanism comprises:

a micro-display.

11. The apparatus of claim 10 wherein the reticle pattern is a software-generated virtual reticle pattern with its dimension determined by the focusing condition or the optical magnification of the handheld eye imaging device.

12. The apparatus of claim 11 wherein the virtual reticle pattern also has overlapping previously recorded images or features that would be used for alignment or comparison.

13. The apparatus of claim 8 wherein the handheld eye imaging device is a RetCam eye imaging system.

14. The apparatus of claim 8 further comprising a calibration means to provide improved measurement accuracy.

15. The apparatus of claim 8 wherein the eye and/or reticle image is projected and/or relayed using optical radiation within the visible spectrum.

16. The apparatus of claim 8 wherein the eye and/or reticle image is projected using optical radiation outside the visible spectral range.

17. The apparatus of claim 8 wherein the reticle pattern includes a pattern of thin wires with tick-marks.

* * * * *